United States Patent
Choi et al.

(10) Patent No.: US 9,261,455 B2
(45) Date of Patent: Feb. 16, 2016

(54) CAPILLARY MICROCUVETTE HAVING DOUBLE LOADING MEANS

(75) Inventors: Eui Yul Choi, Chuncheon-si (KR); Ki Bong Nham, Seoul (KR); Byeong Chul Kim, Chuncheon-si (KR); Ki Tae Park, Chuncheon-si (KR); Cheol Min Kim, Namyangiu-si (KR)

(73) Assignee: BODITECH MED INC., Gangwon-Do (KR)

( * ) Notice: Subject to any disclaimer, the term of this patent is extended or adjusted under 35 U.S.C. 154(b) by 0 days.

(21) Appl. No.: 14/238,191

(22) PCT Filed: Aug. 14, 2012

(86) PCT No.: PCT/KR2012/006465
§ 371 (c)(1),
(2), (4) Date: Feb. 10, 2014

(87) PCT Pub. No.: WO2013/025036
PCT Pub. Date: Feb. 21, 2013

(65) Prior Publication Data
US 2014/0219886 A1 Aug. 7, 2014

(30) Foreign Application Priority Data
Aug. 16, 2011 (KR) ........................ 10-2011-0080964

(51) Int. Cl.
*G01N 33/00* (2006.01)
*G01N 21/11* (2006.01)
(Continued)

(52) U.S. Cl.
CPC .............. *G01N 21/11* (2013.01); *A61B 5/1405* (2013.01); *A61B 5/1411* (2013.01); *A61B 5/150022* (2013.01); *A61B 5/150343* (2013.01); *B01L 3/502715* (2013.01); *A61B 5/14551* (2013.01); *A61B 10/0045* (2013.01); *A61B 2562/0295* (2013.01); *B01L 2200/027* (2013.01);
(Continued)

(58) Field of Classification Search
CPC ................ A61B 2562/0295; B01L 2200/027; B01L 2400/0406
See application file for complete search history.

(56) References Cited

U.S. PATENT DOCUMENTS 4,696,797 A * 9/1987 Kelton ........................ 422/534
5,674,457 A 10/1997 Williamsson et al. ........ 422/102
(Continued)

FOREIGN PATENT DOCUMENTS

JP 2941063 B2 8/1999
KR 10-2011-0041423 A 4/2011

OTHER PUBLICATIONS

International search Report mailed Jan. 20, 2013, issued in corresponding International Application No. PCT/KR2012/006465.

*Primary Examiner* — Sam P Siefke
(74) *Attorney, Agent, or Firm* — Stein IP, LLC (57) ABSTRACT

The present invention relates to a capillary microcuvette, the microcuvette comprises a body member having two plates and a cavity formed within the body, the cavity being defined by two opposing inner surfaces of the two plates of the body member, a portion of the cavity defining a detection zone, a capillary inlet being provided at one end of the body member that is communicated with the cavity, a sample slot being provided at a portion of the body member in which the capillary inlet is not formed, the sample slot being communicated with the cavity. The present microcuvette improves user convenience by providing dual application means of applying a specimen directly from a fingertip or using a pipette.

11 Claims, 8 Drawing Sheets

(51) Int. Cl.
  *A61B 5/15* (2006.01)
  *B01L 3/00* (2006.01)
  *A61B 5/1455* (2006.01)
  *A61B 10/00* (2006.01)

(52) U.S. Cl.
  CPC .. *B01L2300/0825* (2013.01); *B01L 2400/0406* (2013.01)

(56) References Cited

U.S. PATENT DOCUMENTS

| | | | |
|---|---|---|---|
| 6,592,815 B1 * | 7/2003 | Zimmer | 422/412 |
| 2004/0028558 A1 * | 2/2004 | Pollock et al. | 422/57 |
| 2007/0081155 A1 | 4/2007 | Schembri et al. | 356/246 |
| 2009/0185957 A1 | 7/2009 | Assmann et al. | 422/102 |
| 2009/0219527 A1 | 9/2009 | Hulme et al. | 356/319 |

* cited by examiner

CAPILLARY MICROCUVETTE HAVING DOUBLE LOADING MEANS

CROSS-REFERENCE TO RELATED APPLICATIONS

This application is a national phase application International Patent Application No. PCT/KR2012/006465, filed on Aug. 14, 2012, which claims the benefit of Korean Patent Application No. 10-2011-0080964, filed Aug. 16, 2011, in the Korean Intellectual Property Office, the disclosure of which are incorporated herein.

TECHNICAL FIELD

The present invention generally relates to a microcuvette, and more particularly, to a microcuvette having dual sampling means by which direct application of a specimen into the microcuvette or injection of a specimen into the microcuvette using a pipette is possible.

BACKGROUND

Generally capillary microcuvettes are used to perform an optical analysis on the liquid specimen which has been processed in a separate reaction with a proper reagent after it being collected, or to perform an optical analysis on the specimen directly after the collection.

For example, the conventional capillary microcuvettes have been used to optically detect hemoglobin in a blood sample. One example of such is disclosed in Japanese Patent (JP) No. 10-2941063, according to which, the prior art microcuvette is composed of a body member having two flat sheets, and a cavity formed in the inner surfaces of the body member. Also a detection zone is located at one portion of the cavity and is formed by the two inner surfaces separated at a certain distance. The cavity has an outer peripheral portion having a sample inlet and an inner peripheral portion having a channel that has a higher capillary force than the detection zone. Thus blood is introduced through the sample inlet and then blood moves to the detection zone for optical analysis.

However, the problem with the conventional microcuvette is that it can apply the blood specimen only through the sample inlet formed therein. This has resulted in the inconvenience that a finger of the subject needs to be aligned with the narrow sample inlet to apply blood to the microcuvette. The conventional microcuvette is particularly inconvenient because the capillary force to introduce the sample into the detection zone is only generated at a restricted area of the narrow sample inlet.

Further, the conventional microcuvette as described above becomes more difficult to use with blood samples collected beforehand and kept in a tube. For the blood samples in a tube, micropipettes are usually used for dispensing and applying the sample to the microcuvette. However the conventional microcuvette has a structure that is not very much compatible with the micropipettes.

In other words, to introduce or load blood into the conventional microcuvette, the subject needs to contact blood on his or her fingertip directly to the sample inlet of the microcuvette, which is only applicable when blood is provided right before the analysis from the body part such as fingers. However blood samples to be tested are usually collected and kept in a glass tube treated with anticoagulants (hereinafter referred to as a "collection tube"). Thus to take the sample from the collection tube and load it to the conventional microcuvette, extra procedures are required to bring the blood samples to be in contact with the sample inlet before the analysis. For example, one needs to tilt the tube to move its content near the mouth of the tube thus to bring the sample to be in contact with the microcuvette. Or one needs to pipette out some blood sample from the tube and transfer it to a slide glass before a blood sample is loaded onto the conventional microcuvette. However, the former extra procedure as described above may cause biohazardous problems if a blood sample is spilled out during the process. The latter, though it removes a risk of blood spills, may also cause a contamination problem during the process.

Therefore, there is a need to develop a microcuvette which provides a more convenient and safe sample loading system, where a direct loading from the fingertips is possible or the use of micropipette for loading a blood sample into the microcuvette is more conveniently performed.

DETAILED DESCRIPTION OF THE INVENTION

Problems to be Solved

To solve the problems as described above, the purpose of the present invention is to provide a microcuvette for optical analysis of the specimen in which direct introduction or loading of the sample from the source such as fingertip to the microcuvette or the introduction using micropipettes can be more conveniently performed.

SUMMARY OF THE INVENTION

In one aspect, the present disclosure provides a microcuvette for optical analysis of a sample comprising: a body member comprising two planar plates; and a cavity formed within the body member, the cavity being defined by the two opposing inner surfaces of the plates of the body member, a portion of the cavity defining a detection zone, the body member comprising an end portion, a capillary inlet being provided at the end portion and that is communicated with the cavity, a sample slot being provided at a portion of the body member in which the capillary inlet is not formed, the sample slot being communicated with the cavity.

In one embodiment, the cavity has a width which gradually decreases in a direction from the capillary inlet to the sample slot which is recognizable from a top view of the microcuvette.

In other embodiments, the capillary inlet is configured to have a slant.

In still other embodiments, in the present microcuvette, a sample is introduced or loaded through the capillary inlet which generates the specimen flows in a direction from the capillary inlet to the sample slot by capillary action, or the specimen is introduced through the sample slot which generates the sample flows in a direction from the sample slot to the capillary inlet.

In still other embodiments, in the present microcuvette at least one of the two opposing inner surfaces of the plates inwardly protrudes whereby the gap of the cavity at the detection zone is narrower than the rest of the cavity In still other embodiments, the gap of the cavity at the detection zone is from about 0.05 to about 0.25 mm.

In still other embodiments, the present microcuvette or the body member further comprises a handle.

In other aspect, the present disclosure also provides a microcuvette for optical analysis of a sample comprising: a body member comprising two planar plates; and a cavity formed within the body member, the cavity being defined by the two opposing inner surfaces of the plates of the body member, a portion of the cavity defining a detection zone, the body member comprising an end portion, a capillary inlet being provided at the end portion and that is communicated with the cavity, a sample slot being provided at a portion of the body member in which the capillary inlet is not formed, the sample slot being communicated with the cavity, wherein the cavity has a gap, which gradually decreases in a direction from the capillary inlet to the sample slot as it is recognizable in a top view of the microcuvette, the capillary inlet is configured to have a slant, the sample is introduced through the capillary inlet which generates the flow of the sample in a direction from the capillary inlet to the sample slot, or the sample is introduced trough the sample slot which generates the sample flow in a direction from the sample slot to the capillary inlet, at least one of the two opposing inner surfaces of the plates inwardly protrudes whereby the gap of the cavity at the detection zone is narrower than at the rest of the cavity and wherein the gap of the cavity at the detection zone is from about 0.05 to about 0.25 mm.

ADVANTAGEOUS EFFECTS

According to one or more embodiments of the present invention, the microcuvette of the present disclosure improves the user convenience and accuracy of the measurement by providing dual loading means by which the blood can be directly applied to the capillary inlet from finger tips or blood can be conveniently applied from a collection tube to the sample slot using a pipette and the like. Particularly, according to one embodiment of the present disclosure, when applying a specimen using a pipette and the like from a collection tube to the sample slot of the present microcuvette, one does not need to take exactly the same amount of samples for every analysis. Instead, any amount in the range of between about 10 to about 50 µl can be loaded as long as it fills the cavity of the present microcuvette by capillary action.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings.

DETAILED DESCRIPTION OF THE EMBODIMENTS

Reference will now be made in detail to the present embodiments, examples of which are illustrated in the accompanying drawings, wherein like reference numerals refer to the like elements throughout.

Figure 1:
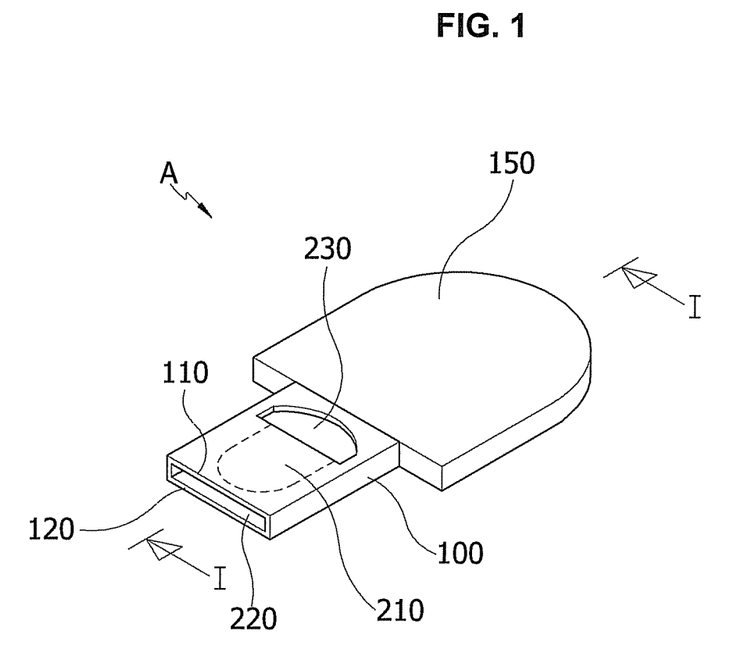
FIG. 1 is a perspective view of a microcuvette according to one example of the present disclosure.
Figure 2:
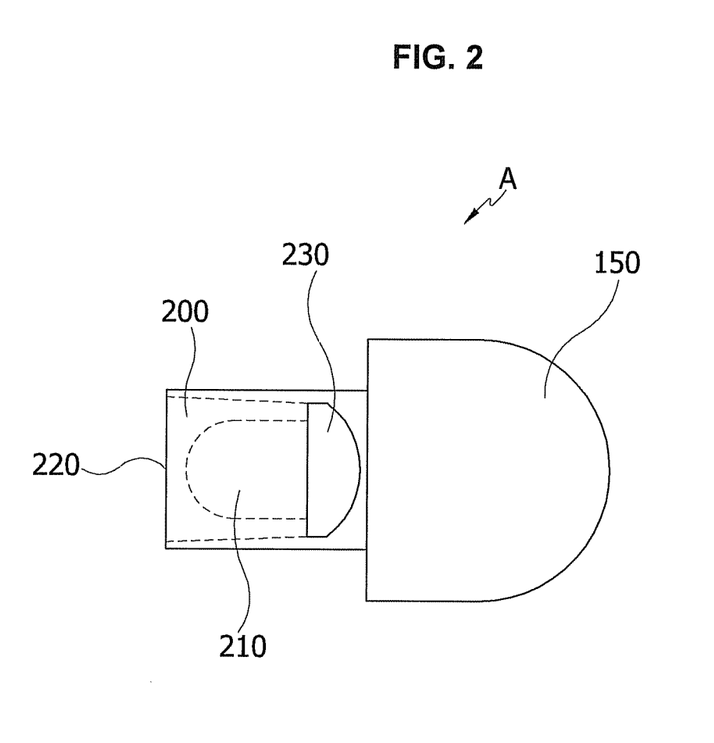
FIG. 2 is a top view of FIG. 1.
Figure 3:
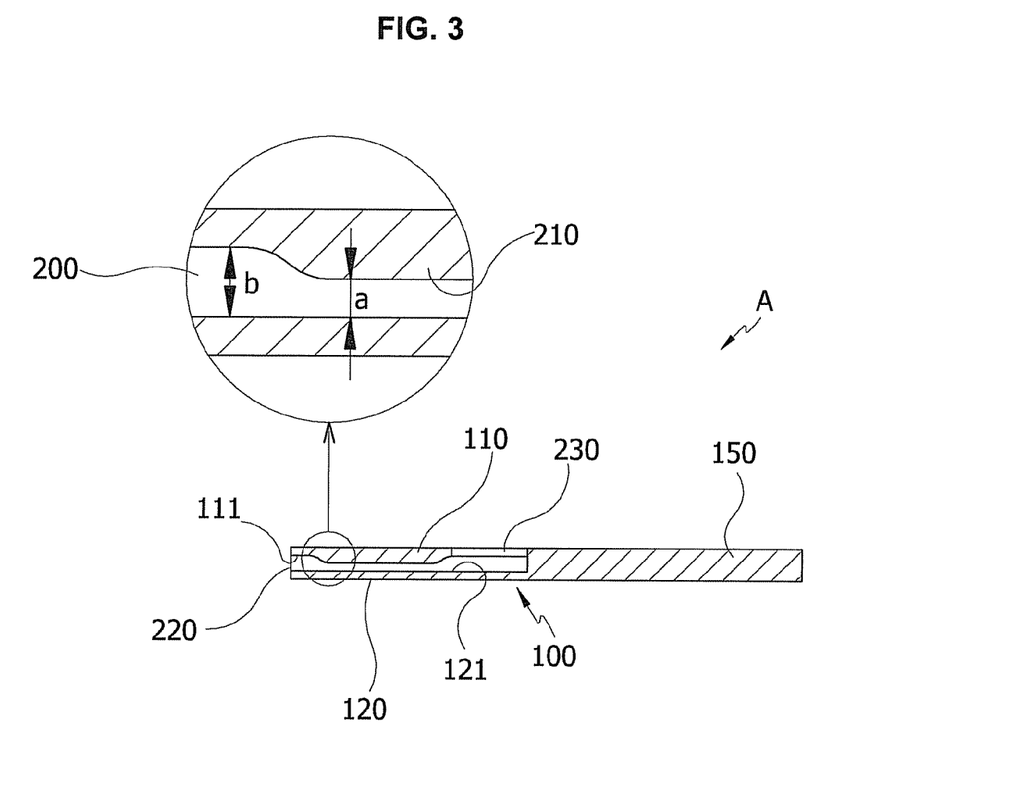
FIG. 3 is a cross-sectional view taken along the line 'I-I' of FIG. 1 in one embodiment.
Figure 4:
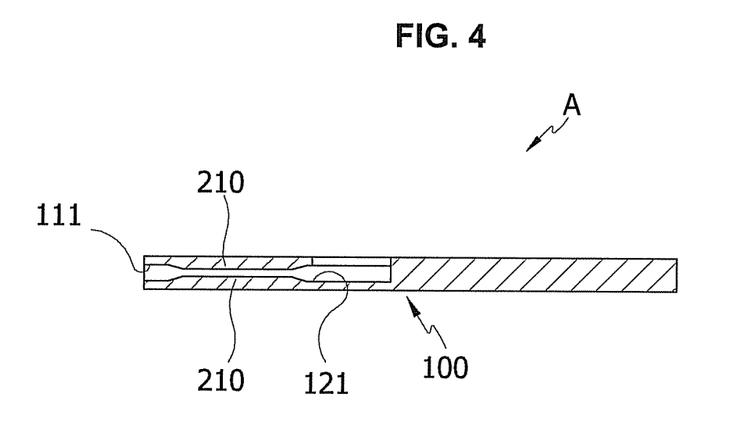
FIG. 4 is a cross-sectional view taken along the line 'I-I' of FIG. 1 in another embodiment.
Figure 5:
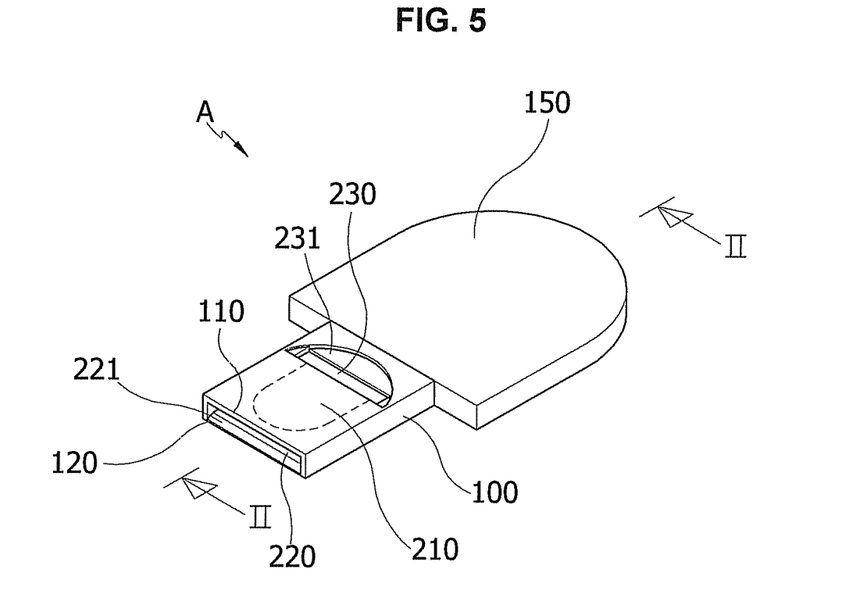
FIG. 5 is a perspective view of a microcuvette according to the other example of the present disclosure.
Figure 6:
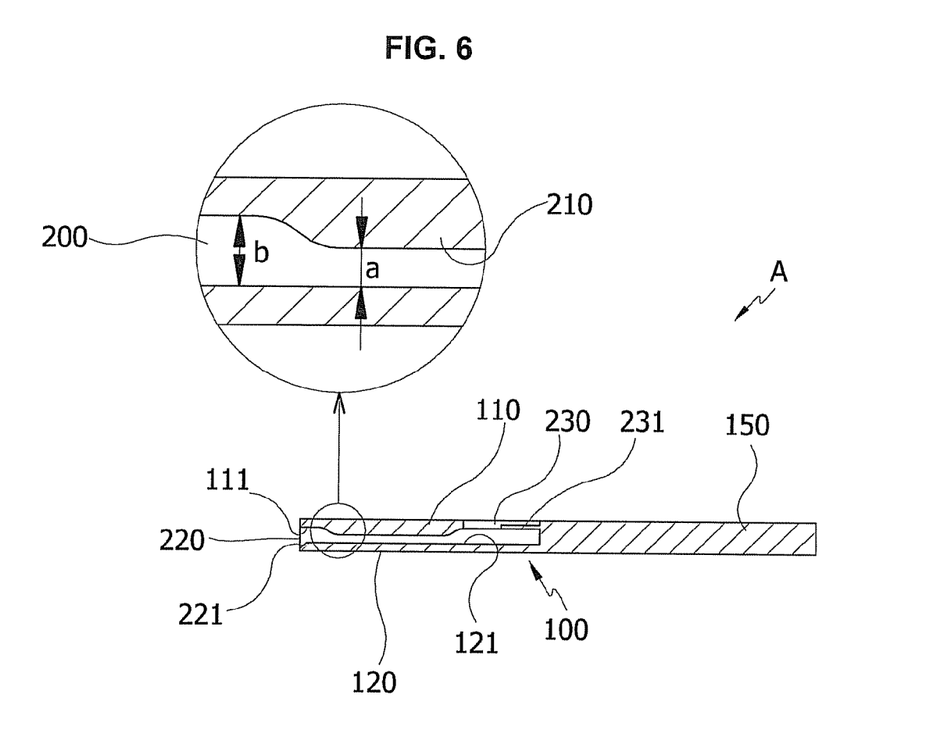
FIG. 6 is a cross-sectional view taken along a line 'II-II' of FIG. 5 in one embodiment.
Figure 7A:
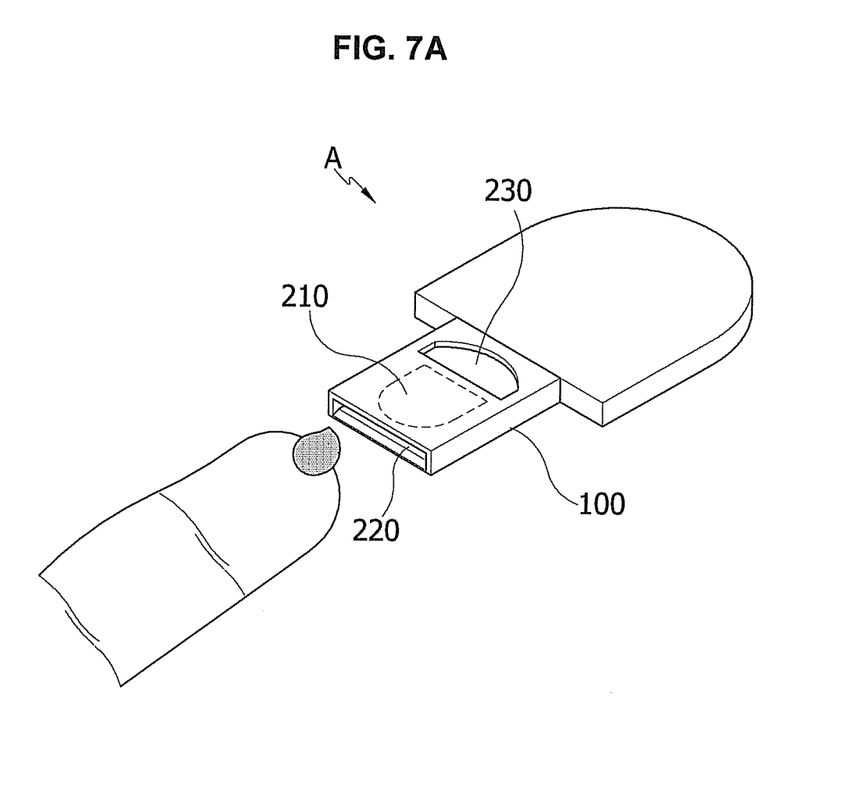
FIGS. 7a and 7b are schematic diagrams each showing one exemplary usage of the present microcuvette.
Figure 7B:
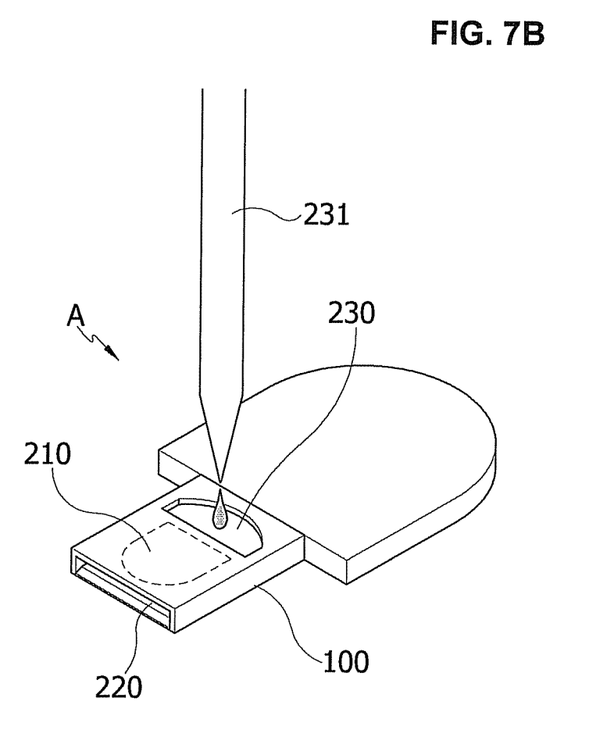

FIG. 1 is a perspective view of a microcuvette according to one example of the present disclosure, FIG. 2 is a top view of FIG. 1, FIG. 3 is a cross-sectional view taken along the line 'I-I' of FIG. 1 in one embodiment, FIG. 4 is a cross-sectional view taken along the line 'I-I' of FIG. 1 in another embodiment, FIG. 5 is a perspective view of a microcuvette according to the other example of the present disclosure, FIG. 6 is a cross-sectional view taken along a line 'II-II' of FIG. 5 in one embodiment, and FIGS. 7a and 7b are schematic diagrams each showing one exemplary usage of the present microcuvette.

As shown in FIGS. 1 through 7b, the present disclosure relates to a capillary microcuvette, the present microcuvette (A) includes a body member 100 having two planar plates and a cavity 200 formed within the body member 100.

A sample or specimen which can be used with the present microcuvette includes, but is not limited to, a fluid biological material such as whole blood, plasma, and serum, urine and a viscous biological material such as feces, expectoration, saliva, and nasal discharge and the like. Viscous materials may be diluted with a suitable liquid such as physiological saline or buffer to introduce the sample to the microcuvette by capillary action.

The cavity 200 is defined by two inner surfaces 111, 121 of two planar plates 110, 120 of the body member 100. As further described hereinafter, at least one or more inner surfaces have may be flat or inwardly protrude to adjust the gap distance of the cavity at the detection zone 210. When the cavity 200 is defined by two inner surfaces 111, 121 of two plates 110, 120 of the body member 100, the outer surface of the plates may be flat and the inner surface may inwardly protrude as needed to adjust the gap distance of the cavity at detection zone 210.

The body member 100 comprises proximal and distal end portions along a longitudinal axis of the body member 100. The capillary inlet 220, which is communicated with the cavity, is formed at one of the end. The sample slot 230, which is communicated with the cavity 230, is provided at the other end portion of the body member at which the capillary inlet 220 is not formed. Further the body member or the microcuvette of the present disclosure may further comprise a handle 150 at one end portion of the body member at which the capillary inlet 220 is not formed.

As shown in FIG. 2, when the body member 100 is viewed from a top side, the cavity 200 is configured to have a width which gradually decreases from a direction of the capillary inlet 220 to the sample slot 230, which facilitates the flow of a sample or specimen loaded by capillary action.

The capillary inlet 220 is communicated with the cavity along a longitudinal axis of the body member 100. The sample slot 230 is formed on one of the two plates 110 or 120 of the body member 100 and communicates with cavity. The cavity is extending from the capillary inlet to the sample slot.

Further the capillary inlet 220 may be configured to have a slant 221 as shown in FIGS. 5 and 6. The slant 221 facilitates an influx of sample loaded and also the sample thus introduced is prevented from being outflowed when the excess sample loaded is removed from the capillary inlet 220.

Further sample slot 230 may be configured to have a recessed portion 231.

As such, the introduction of a specimen such as blood through the capillary inlet 220 generates a flow or a movement of the sample in a direction from the capillary inlet 220 to the sample slot 230, which results in the sample loaded being transported at the detection zone 210. Or when a sample or a specimen such as blood is applied at the sample slot 230, a flow or a movement of the sample is generated in a direction from the capillary slot to the capillary inlet 220, which results in the sample being transported at the detection zone 210.

That is to say, the convenience in analysis is improved because the sample such as blood may be applied or introduced either through the capillary inlet 220 or the sample slot 230, where in both cases, the sample applied is transported to the detection zone 210, at which the sample is analyzed by measuring the absorbance after illuminating the detection zone 210 with a light with an appropriate wavelength.

Also, the detection zone 210 is formed at a portion of the cavity 200. In one embodiment, at least one of the inner surfaces 111, 121 of the detection zone 210 inwardly protrudes as shown in FIGS. 3 and 4.

Meanwhile, the plates (110, 120) or the body member 100 comprising the two plates (110, 120) is made of various materials that may be light transmittable for optical measurements. Alternatively, only the detection zone may be made of a light transmittable material and the rest of the microcuvette is made of a non-transmittable material.

When the detection zone or the entire microcuvette is made of a light transmittable material, appropriate materials may be selected by one of the skilled persons in the art considering the types of light illuminated and/or samples. For example, polymeric materials such as glass or plastic may be used. For example polystyrene may be used, but is not limited thereto. When visible lights are employed, materials such as polystyrene may be used.

Meanwhile, the gap or gap distance '(a)' of the cavity at detection zone 210 is narrower than the gap '(b)' at the rest of the cavity 200. The detection zone 210 is to detect an analyte of interest present in a sample by optical methods using light illumination and it determines a distance of the optical passage. The gap '(a)' of the cavity at the detection zone may vary depending on the types of sample analyzed, the types or characteristics of the analyte of interest, or the types or intensity of the light used for illumination. For example, the gap '(a)' may be from about 0.05 to about 0.25 mm in length, and the light being used for illumination has a wavelength of about 500 to 550 nm. In one embodiment, the gap is about 0.2 mm. In other embodiments, the gap is about 0.1 mm. The gap of the cavity other than the detection zone may be ranged from about 0.5 mm to about 1.5 mm.

Also the difference in the gap distance between the detection zone and the rest of the cavity area prevents generation or trapping of air bubbles in the sample loaded within the detection zone 210. When the blood containing air bubbles is being loaded to the present microcuvette, the bubbles introduced are removed as the sample applied is spreading out to the detection zone 201 at which the gap becomes narrower than that of the rest of the cavity. Thus by removing the air bubbles at the detection zone, the accuracy at the measurement or detection level is further improved.

The detection zone 210 may be formed of various shapes such a polygon or a circle or a simple closed curve, when viewed from the top.

Also as shown in FIGS. 7a and 7b, with the present microcuvette for optical analysis having dual loading means, a sample such as blood may be loaded to the capillary inlet 220 directly from a fingertip as shown in FIG. 7a, or a sample may be loaded using pipette 231 through the sample slot 230, through which the user convenience is improved.

While a few exemplary embodiments of the present invention have been shown and described, it would be appreciated by those skilled in the art that changes may be made to these exemplary embodiments without departing the principles and spirit of the invention, the scope of which is defined by the claims and their equivalents.

For example, in the foregoing description, the capillary microcuvette may be used for measuring not only the amounts of haemoglobins in a sample, but also the amount of other analytes such as glucose, urea, nitrogen and proteins. Not only blood but also other various samples may be used with the present capillary microcuvette. The microcuvette of the present invention is used in medical diagnosis/detection fields, but it may also be applied to various other industrial fields where the present microcuvette is applicable.

[Description of the Numerals used]

A- Capillary microcuvette of the present invention  100- body member
110, 120 - plates              111, 121- Inner surfaces of the plates
150 - handle                   200 - cavity
210 - detection zone           220 - capillary inlet
221 - slant                    230 - sample slot.

What is claimed is:

1. A capillary microcuvette for optical analysis of a sample, the microcuvette comprising:
   a body member comprising two planar plates; and
   a cavity formed within the body member,
   wherein the cavity is defined by the two opposing inner surfaces of the plates of the body member, and a portion of the cavity defines a detection zone,
   wherein the body member comprises an end portion, a capillary inlet provided at the end portion to be communicated with the cavity, and a sample slot provided at a portion of the body member in which the capillary inlet is not formed, the sample slot being communicated with the cavity,
   wherein at least one of the two opposing inner surfaces of the plates inwardly protrudes whereby a gap of the cavity in a direction perpendicular to the two plates at the detection zone is narrower than a gap of the cavity in the direction perpendicular to the two plates in the rest of the cavity.

2. The capillary microcuvette of claim 1, wherein the cavity has a width which gradually decreases in a direction from the capillary inlet to the sample slot as recognized from a top view of the microcuvette.

3. The capillary microcuvette of claim 1, wherein the capillary inlet is configured to have a slant.

4. The capillary microcuvette of claim 1, wherein the sample is introduced through the capillary inlet which generates a flow of the sample in a direction from the capillary inlet to the sample slot, or the sample is introduced through the sample slot which generates a flow of the sample in a direction from the sample slot to the capillary inlet.

5. The capillary microcuvette of claim 1, wherein the gap is from 0.10 to 0.25 mm.

6. The capillary microcuvette of claim 1, wherein the body member further comprises a handle.

7. The capillary microcuvette of claim 2, wherein the sample is introduced through the capillary inlet which generates a flow of the sample in a direction from the capillary inlet to the sample slot, or the sample is introduced through the sample slot which generates a flow of the sample in a direction from the sample slot to the capillary inlet.

8. The capillary microcuvette of claim 2, wherein the body member further comprises a handle.

9. The capillary microcuvette of claim 3, wherein the sample is introduced through the capillary inlet which generates a flow of the sample in a direction from the capillary inlet to the sample slot, or the sample is introduced through the sample slot which generates a flow of the sample in a direction from the sample slot to the capillary inlet.

10. The capillary microcuvette of claim 3, wherein the body member further comprises a handle.

11. The capillary microcuvette of claim 1, wherein the sample slot comprises a recessed portion.

* * * * *